US006534478B1

(12) United States Patent
Jonczyk et al.

(10) Patent No.: US 6,534,478 B1
(45) Date of Patent: Mar. 18, 2003

(54) CYCLIC AZAPEPTIDES WITH ANGIOGENIC EFFECT

(75) Inventors: Alfred Jonczyk, Darmstadtz (DE); Simon Goodman, Darmstadt (DE); Horst Kessler, Darmstadt (DE); Jochen Wermuth, Darmstadt (DE); Jörg Schmitt, Darmstadt (DE)

(73) Assignee: Merck Patent Gesellschaft Mit, Darmstadt (DE)

( * ) Notice: Subject to any disclaimer, the term of this patent is extended or adjusted under 35 U.S.C. 154(b) by 0 days.

(21) Appl. No.: 09/446,974

(22) PCT Filed: Jun. 29, 1998

(86) PCT No.: PCT/EP98/03955

§ 371 (c)(1),
(2), (4) Date: Mar. 23, 2000

(87) PCT Pub. No.: WO99/01472

PCT Pub. Date: Jan. 14, 1999

(30) Foreign Application Priority Data

Jul. 4, 1997 (DE) .......................... 197 28 524

(51) Int. Cl.$^7$ ...................... A61K 38/00; A61K 38/12; C07K 16/00
(52) U.S. Cl. ...................... 514/9; 514/17; 530/317; 530/329; 530/330
(58) Field of Search ...................... 514/9, 17; 530/317, 530/329, 330

(56) References Cited

FOREIGN PATENT DOCUMENTS

| DE | 19653036 | 6/1998 |
| WO | 9324520 | 12/1993 |
| WO | 95 23811 | 9/1995 |
| WO | 9725343 | 7/1997 |

OTHER PUBLICATIONS

Bowie et al., Science, vol. 247, pp. 1306–1310, 1990.*
Houghten et al., Vaccines 86, Cold Spring Harbor Laboratory, pp. 21–25, 1986.*

* cited by examiner

Primary Examiner—Christopher S. F. Low
Assistant Examiner—Abdel A. Mohamed
(74) Attorney, Agent, or Firm—Millen, White, Zelano & Branigan, P.C.

(57) ABSTRACT

Compounds of the formula I cyclo-(aArg-aGly-aAsp-aX-aY)       I in which aArg, aGly, aAsp, aX and aY have the meanings indicated in claim 1,
and their salts,
can be used as integrin inhibitors, in particular for the prophylaxis and treatment of diseases of the circulation, in thrombosis, cardiac infarct, coronary heart diseases, arteriosclerosis, in pathological processes which are supported or propagated by angiogenesis and in tumour therapy.

8 Claims, No Drawings

CYCLIC AZAPEPTIDES WITH ANGIOGENIC EFFECT

SUMMARY OF THE INVENTION

The invention relates to compounds of the formula I cyclo-(aArg-aGly-aAsp-aX-aY)    I in which
- aArg is Arg or aza-Arg,
- aGly is Gly or aza-Gly,
- aAsp is Asp or aza-Asp,
- aX, aY in each case independently of one another are an amino acid residue selected from a group consisting of Ala, Asn, Asp, Arg, Cys, Gln, Glu, Gly, His, Ile, Leu, Lys, Met, Nle, Orn, Phe, Phg, Pro, Ser, Thr, Tic, Trp, Tyr, Val, NH—Q—CO—
or
the corresponding aza-amino acids,
- Q is alkylene having 1–6 C atoms, where
in at least one of the amino acids mentioned in formula I the $C^\alpha$ carbon is replaced by nitrogen,
the amino acids mentioned can also be derivatized, and the amino acid residues are linked to one another in peptide fashion via the a-amino or aza group and α-carboxyl groups,
and if there are radicals of optically active amino acids and amino acid derivatives, both the D and the L forms are included,
and their salts.

Similar compounds of cyclic peptides are disclosed, for example, in EP 0 632 053, DE 195 38 741 or EP 0 683 173.

DETAILED DESCRIPTION OF THE INVENTION

The invention is based on the object of finding novel compounds having valuable properties, in particular those which can be used for the production of medicaments.

It has been found that the compounds of the formula I and their salts have very valuable pharmacological properties combined with good tolerability. They act especially as integrin inhibitors, in particular inhibiting the interactions of the $\alpha_v$-, $\beta_3$- or $\beta_5$-integrin receptors with ligands, such as, for example, the binding of fibrinogen to the $\beta_3$-integrin receptor. The compounds show particular activity in the case of the integrins $\alpha_v\beta_1$, $\alpha_v\beta_3$, $\alpha_v\beta_5$, $\alpha_{IIb}\beta_3$ and also $\alpha_v\beta_6$ and $\alpha_v\beta_8$, in particular potent selective inhibitors of the vitronectin receptor $\alpha_v\beta_3$ have been found.

This action can be demonstrated, for example, by the method which is described by J. W. Smith et al. in J. Biol. Chem. 265, 12267–12271 (1990). The dependence of the origin of angiogenesis on the interaction between vascular integrins and extracellular matrix proteins is described by P. C. Brooks, R. A. Clark and D. A. Cheresh in Science 264, 569–71 (1994).

The possibility of the inhibition of this interaction and thus for the initiation of apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I, which block the interaction of integrin receptors and ligands, such as, for example, of fibrinogen on the fibrinogen receptor (glycoprotein IIb/IIIa), prevent, as GPIIb/IIIa antagonists, the spread of tumour cells by metastasis. This is confirmed by the following observations:

The compounds can inhibit the binding of metalloproteinases to integrins and thus prevent the cells being able to utilize the enzymatic activity of the proteinase. An example is to be found in the inhibitability of the binding of MMP-2 (matrix metalloproteinase-2) to the vitronectin receptor $\alpha_v\beta_3$ by a cyclo-RGD peptide, as described in P. C. Brooks et al., Cell 85, 683–693 (1996).

The spread of tumour cells from a local tumour into the vascular system takes place through the formation of microaggregates (microthrombi) by interaction of the tumour cells with blood platelets. The tumour cells are screened by protection in the microaggregate and are not recognized by the cells of the immune system. The microaggregates can fix to vascular walls, by means of which a further penetration of tumour cells into the tissue is facilitated. Since the formation of the microthrombi is mediated by fibrinogen formation on the fibrinogen receptors on activated blood platelets, the GPIIa/IIIb antagonists can be regarded as effective metasis inhibitors.

The compounds of the formula I can be employed as pharmaceutical active compounds in human and veterinary medicine, in particular for the prophylaxis and/or therapy of thrombosis, myocardial infarct, arteriosclerosis, inflammations, apoplexy, angina pectoris, oncoses, osteolytic diseases such as osteoporosis, pathologically angiogenic diseases such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, multiple sclerosis, viral infection, bacterial infection, fungal infection, in acute kidney failure and in wound healing for supporting the healing processes.

The compounds of the formula I can be employed as substances having antimicrobial activity in operations where biomaterials, implants, catheters or heart pacemakers are used.

They have an antiseptic action here. The efficacy of the antimicrobial activity can be demonstrated by the procedure described by P. Valentin-Weigund et al., in Infection and Immunity, 2851–2855 (1988).

Since the compounds of the formula I are inhibitors of fibrinogen binding and thus ligands of the fibrinogen receptors on blood platelets, they can be used in vivo as diagnostics for the detection and localization of thrombi in the vascular system, provided they are substituted, for example, by a radioactive or UV-detectable residue.

The compounds of the formula I can be used as inhibitors of fibrinogen binding and as effective auxiliaries for the study of the metabolism of blood platelets in different activation stages or of intra-cellular signal mechanisms of the fibrinogen receptor. The detectable unit of a "label" to be incorporated, e.g. isotopic labelling by $^3$H, allows, after binding to the receptor, the mechanisms mentioned to be investigated.

In the compounds of the formula I, the amino acids present can be modified such that the $C^\alpha$ carbon is replaced by nitrogen, with retention of the side chain. In this case, these are so-called aza-amino acids. For example, in the aza-tripeptide below, consisting of the amino acids arginine, glycine and aspartic acid, the $C^\alpha$ carbon of the glycine is replaced by nitrogen.

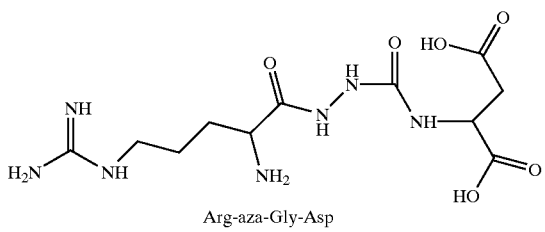

Arg-aza-Gly-Asp

In the compounds of the formula I according to the invention, at least one amino acid is always present as an aza-amino acid.

The abbreviations of amino acid residues listed above and below stand for the radicals of the following amino acids:

| | |
|---|---|
| Ala | alanine |
| Asn | asparagine |
| Asp | aspartic acid |
| Arg | arginine |
| Cys | cysteine |
| Gln | glutamine |
| Glu | glutamic acid |
| Gly | glycine |
| His | histidine |
| homo-Phe | homo-phenylalanine |
| Ile | isoleucine |
| Leu | leucine |
| Lys | lysine |
| Met | methionine |
| Nle | norleucine |
| Orn | ornithine |
| Phe | phenylalanine |
| Phg | phenylglycine |
| 4-Hal-Phe | 4-halophenylalanine |
| Pro | proline |
| Sar | sarcosine (N-methylglycine) |
| Ser | serine |
| Tic | tetrahydroisoquinoline-3-carboxylic acid |
| Thr | threonine |
| Trp | tryptophan |
| Tyr | tyrosine |
| Val | valine. |

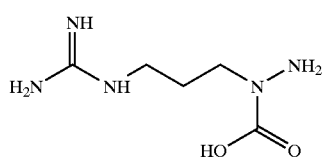

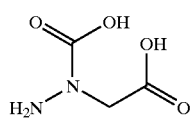

| | |
|---|---|
| Ac | acetyl |
| Boc | tert-butoxycarbonyl |
| CBZ or Z | benzyloxycarbonyl |
| DCCI | dicyclohexylcarbodiimide |
| DIPEA | diisopropylethylamine |
| DMF | dimethylformamide |
| EDCI | N-ethyl-N,N'-(dimethylaminopropyl) carbodiimide |
| Et | ethyl |
| Fmoc | 9-fluorenylmethoxycarbonyl |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| NMP | N-methylpyrrolidone |
| HONSu | N-hydroxysuccinimide |
| OBzl | benzyl ester |
| OtBu | tert-butyl ester |
| Oct | octanoyl |
| OMe | methyl ester |
| OEt | ethyl ester |
| Pbf | 2,2,4,6,7-pentamethyldihydrobenzofuran-5-sulfonyl |
| POA | phenoxyacetyl |
| Sal | salicyloyl |
| TBTU | O-(1H-benzotriazol-1-yl)-N,N,N',N'-tetramethyluronium tetrafluoroborate |
| TFA | trifluoroacetic acid |
| Trt | trityl (triphenylmethyl). |

If the abovementioned amino acids can occur in several enantiomeric forms, then above and below, e.g. as a constituent of the compounds of the formula I, all these forms and also their mixtures (e.g. the DL forms) are included. Furthermore, the amino acids can be provided, e.g. as a constituent of compounds of the formula I, with corresponding protective groups which are known per se.

So-called prodrug derivatives are also included in the compounds according to the invention, i.e. compounds of the formula I, modified with, for example, alkyl or acyl groups, sugars or oligopeptides, which are rapidly cleaved in the body to the active compounds according to the invention. These also include biodegradable polymer derivatives of the compounds according to the invention, as is described, for example, in Int. J. Pharm. 115, 61–67 (1995).

Amino acids whose configuration is not specifically indicated have the (S) or (L) configuration.

The invention further relates to a process for the preparation of compounds of the formula I according to claim 1 and of their salts, characterized in that (a) a compound of the formula II $$H—Z—OH \qquad II$$

in which
Z is —aArg-aGly-aAsp-aX-aY—, —aGly-aAsp-aX-aY-aArg, —aAsp-aX-aY-aArg-aGly—, —aX-aY-aArg-aGly-aAsp— or —aY-aArg-aGly-aAsp-aX—,
and aArg, aGly, aAsp, aX and aY have the meanings indicated in claim 1,
or a reactive derivative of a compound of the formula II is treated with a cyclizing agent,
or b) a compound of the formula I is set free from one of its functional derivatives by treating with a solvolysing or hydrogenolysing agent, and/or in that a basic or acidic compound of the formula I is converted into one of its salts by treating with an acid or base.

Above and below, the radicals aArg, aGly, aAsp, aX and aY have the meanings indicated in the formulae I and II, if not expressly stated otherwise.

In the above formulae, alkyl is preferably methyl, ethyl, propyl, isopropyl, butyl, isoburyl, sec-butyl or tert-butyl, and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1-or 2-ethylbutyl, 1-ethyl-1-methylpropyl, 1-ethyl-2-methylpropyl, 1,1,2- or 1,2,2-trimethylpropyl.

Alkylene is preferably methylene, ethylene, propylene, butylene, pentylene or hexylene.

The amino acids and amino acid residues mentioned can also be derivatized, the N-methyl, N-ethyl, N-propyl, N-benzyl or C,-methyl derivatives being preferred. Derivatives of Asp and Glu are furthermore preferred, in particular the methyl, ethyl, propyl, butyl, tert-butyl, neopentyl or benzyl esters of the side chain carboxyl groups, and further also derivatives of Arg, which can be substituted on the —NH—C(=NH)—NH$_2$ group by an acetyl, benzoyl, methoxycarbonyl or ethoxycarbonyl radical.

Amino protective group preferably denotes acetyl, propionyl, butyryl, phenylacetyl, benzoyl, toluyl, POA, methoxycarbonyl, ethoxycarbonyl, 2,2,2-trichloro-ethoxycarbonyl, Boc, 2-iodoethoxycarbonyl, CBZ ("carbobenzoxy"), 4-methoxybenzyloxycarbonyl, Fmoc, Mtr or benzyl.

The compounds of the formula I can have one or more chiral centres and therefore occur in various stereoisomeric forms. The formula I includes all these forms.

Accordingly, the invention relates in particular to those compounds of the formula I in which at least one of the radicals mentioned has one of the preferred meanings indicated above. Some preferred groups of compounds can be expressed by the following subformulae Ia to Ic, which correspond to the formula I and in which the radicals not designated in greater detail have the meaning indicated under the formula I, but in which in Ia) aArg is Arg,
aGly is aza-Gly,
aAsp is Asp
aX, aY in each case independently of one another are an amino acid residue selected from a group consisting of Ala, Asn, Asp, Arg, Cys, Gln, Glu, Gly, His, Ile, Leu, Lys, Met, Phe, Pro, Ser, Thr, Trp, Tyr, Val
or
the corresponding aza-amino acids, and the abovementioned amino acids can also be derivatized;

in Ib) aArg is Arg,
aGly is aza-Gly,
aAsp is Asp
aX is Gly, Phe, D-Phe or aza-Phe and
aY is Gly, Val, Leu, Pro, D-Val, D-Leu or D-Pro
or
the corresponding aza-amino acids, and the amino acids mentioned can also be derivatized;

in Ic) aArg is Arg,
aGly is aza-Gly,
aAsp is Asp
aX is Gly, Phe or D-Phe and
aY is Gly, N-benzyl-Gly, Lys, D-Lys, Val, D-Val,
or
the corresponding aza-amino acids,
and the amino acids mentioned can also be derivatized;

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. In this case, use can also be made of variants which are known per se but not mentioned here in greater detail.

If desired, the starting substances can also be formed in situ such that they are not isolated from the reaction mixture, but are immediately reacted further to give the compounds of the formula I.

Compounds of the formula I can preferably be obtained by cyclization of compounds of the formula II under the conditions of a peptide synthesis. In this case, the reaction is expediently carried out by customary methods of peptide synthesis, such as are described, for example, in Houben-Weyl, l.c., Volume 15/II, pages 1 to 806 (1974).

The reaction preferably takes place in the presence of a dehydrating agent, e.g. of a carbodiimide such as DCCI or EDCI, and further, for example, propanephosphonic anhydride (cf. Angew. Chem. 92, 129 (1980)), diphenylphosphoryl azide or 2-ethoxy-N-ethoxy-carbonyl-1,2-dihydroquinoline, in an inert solvent, e.g. a halogenated hydrocarbon such as dichloromethane, an ether such as tetrahydrofuran or dioxane, an amide such as DMF or dimethylacetamide, a nitrile such as acetonitrile, in dimethyl sulfoxide or in the presence of these solvents, at temperatures between approximately −10 and 40°, preferably between 0 and 30°. In order to promote intramolecular cyclization ahead of intermolecular peptide bonding, it is expedient to work in dilute solutions.

Depending on the conditions used the reaction time is between a few minutes and 14 days.

Instead of compounds of the formula II, it is also possible to employ derivatives of compounds of the formula II, preferably a preactivated carboxylic acid, or a carboxylic acid halide, a symmetrical or mixed anhydride or an active ester. Radicals of this type for the activation of the carboxyl group in typical acylation reactions are described in the literature (e.g. in the standard works such as Houben-Weyl, Methoden der organischen Chemie [Methods of Organic Chemistry], Georg-Thieme-Verlag, Stuttgart). Activated esters are expediently formed in situ, e.g. by addition of HOBt or N-hydroxysuccinimide.

As a rule, the reaction is carried out in an inert solvent, when using a carboxylic acid halide in the presence of an acid-binding agent, preferably of an organic base such as triethylamine, dimethylaniline, pyridine or quinoline.

The addition of an alkali metal or alkaline earth metal hydroxide, carbonate or bicarbonate or of another salt of a weak acid of the alkali metals or alkaline earth metals, preferably of potassium, sodium, calcium or caesium, may also be favourable.

As a rule, the starting substances of the formula II are novel. They can be prepared by known methods of peptide synthesis. Linear peptides can be synthesized, for example, according to Merrifield (Angew. Chem. 97, 801–812 1985) on a solid phase, a swellable polystyrene resin.

The compounds of the formula I can further be obtained by setting them free from their functional derivatives by solvolysis, in particular hydrolysis, or by hydrogenolysis.

Preferred starting substances for the solvolysis or hydrogenolysis are those which, instead of one or more free amino and/or hydroxyl groups, contain corresponding protected amino and/or hydroxyl groups, preferably those which, instead of an H atom which is bonded to an N atom, carry an amino protective group, e.g. those which correspond to the formula I but instead of an NH$_2$ group contain an NHR' group (in which R' is an amino protective group, e.g. Boc or CBZ).

Starting substances are furthermore preferred which, instead of the H atom of a hydroxyl group, carry a hydroxyl protective group, e.g. those which correspond to the formula I but instead of a hydroxyphenyl group contain an R"O-phenyl group (in which R" is a hydroxyl protective group).

A plurality of—identical or different—protected amino and/or hydroxyl groups can also be present in the molecule of the starting substance. If the protective groups present are different from one another, in many cases they can be selectively removed.

The expression "amino protective group" is generally known and relates to groups which are suitable for protecting (for blocking) an amino group from chemical reactions, but which are easily removable after the desired chemical reaction has been carried out at other positions in the molecule. Typical of such groups are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, Boc, 2-iodoethoxycarbonyl; aralkyloxycarbonyl such as CBZ ("carbobenzoxy"), 4-methoxybenzyloxycarbonyl, Fmoc; arylsulfonyl such as Mtr. Preferred amino protective groups are Boc and Mtr, and further CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other positions in the molecule. Typical of such groups are the abovementioned unsubstituted or substituted aryl, aralkyl or acyl groups, and furthermore also alkyl groups. The nature and size of the hydroxyl protective groups is not critical, since they are removed again after the desired chemical reaction or reaction sequence; groups having 1–20, in particular 1–10, C atoms are preferred. Examples of hydroxyl protective groups are, inter alia, benzyl, p-nitrobenzoyl, p-toluenesulfonyl, tert-butyl and acetyl, benzyl and tert-butyl being particularly preferred. The COOH groups in aspartic acid and glutamic acid are preferably protected in the form of their tert-butyl esters (e.g. Asp(OBut)).

The compounds of the formula I are set free from their functional derivatives—depending on the protective group used—e.g. using strong acids, expediently using TFA or perchloric acid, but also using other strong inorganic acids such as hydrochloric acid or sulfuric acid, strong organic carboxylic acids such as trichloroacetic acid or sulfonic acids such as benzene-or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, and furthermore also alcohols such as methanol, ethanol or isopropanol, and also water. Mixtures of the abovementioned solvents are furthermore suitable. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°, preferably the cleavage is carried out between 15 and 30° (room temperature).

The groups Boc, OBut and Mtr can, for example, preferably be removed using TFA in dichloromethane or using approximately 3 to 5 N HCl in dioxane at 15–30°, the Fmoc group using an approximately 5 to 50% solution of dimethylamine, diethylamine or piperidine in DMF at 15–30°.

The trityl group is employed for the protection of the amino acids histidine, asparagine, glutamine and cysteine. Removal is carried out, depending on the desired final product, using TFA/10% thiophenol, the trityl group of all amino acids mentioned being removed, when using TFA/anisole or TFA/thioanisole only the trityl group of His, Asn and Gln being removed, while it remains on the Cys side chain.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° and 1–10 bar. Hydrogenolysis of the CBZ group is readily carried out, for example, on 5 to 10% Pd/C in methanol or using ammonium formate (instead of hydrogen) on Pd/C in methanol/DMF at 20–30°.

A base of the formula I can be converted into the associated acid addition salt using an acid, for example by reaction of equivalent amounts of the base and of the acid in an inert solvent such as ethanol and subsequent evaporation. In particular, acids which yield physiologically acceptable salts are suitable for this reaction. Thus inorganic acids can be used, e.g. sulfuric acid, nitric acid, hydrohalic acids such as hydrochloric acid or hydrobromic acid, phosphoric acids such as orthophosphoric acid, sulfamic acid, and furthermore organic acids, in particular aliphatic, alicyclic, araliphatic, aromatic or heterocyclic mono-or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Possible salts in this case are, in particular, the sodium, potassium, magnesium, calcium and ammonium salts, and furthermore substituted ammonium salts, e.g. the dimethyl-, diethyl- or diisopropylammonium salts, monoethanol-, diethanol- or diisopropylammonium salts, cyclohexyl- or dicyclohexylammonium salts, dibenzylethylenediammonium salts, and furthermore, for example, salts with arginine or lysine.

The invention further relates to the use of the compounds of the formula I and/or their physiologically acceptable salts for the production of pharmaceutical preparations, in particular in a non-chemical way. In this context, they can be brought into a suitable dose form together with at least one solid, liquid and/or semi-liquid excipient or auxiliary and, if appropriate, in combination with one or more other active compounds.

The invention furthermore relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration, topical application or administration in the form of an inhalation spray and do not react with the novel compounds, for example water, vegetable oils, benzyl alcohols, alkylene glycols, polyethylene glycols, glyceryl triacetate, gelatin, carbohydrates such as lactose or starch, magnesium stearate, talc, petroleum jelly. In particular, tablets, pills, coated tablets, capsules, powders, granules, syrups, juices or drops are used for oral administration, suppositories are used for rectal administration, solutions, preferably oily or aqueous solutions, and furthermore suspensions, emulsions or implants are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. For administration as an inhalation spray, sprays can be used which contain the active compound either dissolved or suspended in a propellant or propellant mixture (e.g. $CO_2$ or chlorofluorohydrocarbons). Expediently, the active compound is in this case used in micronized form, it being possible for one or more additional physiologically tolerable solvents, e.g. ethanol, to be present. Inhalation solutions can be administered with the aid of customary inhalers.

The compounds of the formula I and their physiologically acceptable salts can be used as integrin inhibitors in the control of illnesses, in particular of thromboses, cardiac infarct, coronary heart diseases, arteriosclerosis, tumours, osteoporosis, inflammations and infections.

The compounds of the formula I according to claim 1 and/or their physiologically acceptable salts are also used in pathological processes which are supported or propagated by angiogenesis, in particular in tumours or rheumatoid arthritis.

In this case, the substances according to the invention can as a rule be administered in analogy to other known, commercially available peptides, but in particular in analogy to the compounds described in U.S. Pat. No. 4,472,305, preferably in doses between approximately 0.05 and 500 mg, in particular between 0.5 and 100 mg per dose unit. The daily dose is preferably between approximately 0.01 and 2 mg/kg of body weight. The specific dose for each patient depends, however, on all sorts of factors, for example on the efficacy of the specific compound employed, on the age, body weight, general state of health, sex, on the diet, on the time and route of administration, on the excretion rate, pharmaceutical combination and severity of the particular disorder to which the therapy applies. Parenteral administration is preferred.

The compounds of the formula I can furthermore be used as integrin ligands for the preparation of columns for affinity chromatography for the preparation of integrins in pure form. The ligand, i.e. a compound of the formula I, is in this case coupled to a polymeric support via an anchor function, e.g. the carboxyl group of Asp.

Suitable polymeric supports are the polymeric solid phases, preferably having hydrophilic properties, known per se in peptide chemistry, for example crosslinked polysugars such as cellulose, Sepharose or SEPHADEX® (a crosslinked polymer of dextran), acrylamides, polymer based on polyethylene glycol or Tentakel® polymers (anion ion exchangers).

The materials for affinity chromatography for integrin purification are prepared under conditions such as are customary and known per se for the condensation of amino acids.

The compounds of the formula I contain one or more chiral centres and can therefore be present in racemic or in optically active form, Racemates obtained can be separated into the enantiomers mechanically or chemically by methods known per se. Preferably, diastereomers are formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Also advantageous is an enantiomer resolution with the aid of a column packed with an optically active resolving agent (e.g. dinitrobenzoylphenylglycine); a suitable eluent is, for example, a mixture of hexane/isopropanol/acetonitrile e.g. in the volume ratio 82:15:3.

Of course, it is also possible to obtain optically active compounds of the formula I by the methods described above by using starting substances which are already optically active.

All temperatures above and below are indicated in ° C. In the following examples, "customary working up" means: if necessary, water is added, the mixture is adjusted, if necessary, to a pH of between 2 and 10, depending on the constitution of the final product, and extracted with ethylacetate or dichloromethane, the organic phase is separated off, dried over sodium sulfate and evaporated, and the residue is purified by chromatography on silica gel and/or by crystallization. $R_f$ values on silica gel; eluent: n-butanol/acetic acid/water 3:1:1 (A), chloroform/memthanol 9:1 (B)

RT—retention time (minutes) on HPLC in the following systems:

column: Nucleosil -5-$C_{18}$ column (250×4; 5 μm); eluents used were gradients of acetonitrile with 0.9% TFA and water with 1.1% TFA (data in each case in per cent by volume of acetonitrile) detection at 220 and 254 nm.

The separation of the diastereomers is preferably carried out under the conditions indicated.

Mass spectrometry (MS): FAB (Fast Atom Bombardment) $(M+H)^+$.

EXAMPLE 1

1 equivalent of DIPEA and 200 mg of p-nitrophenyl chloroformate (Cl—CO-Pnp) in 10 ml of dichloromethane are added to a solution of 280 mg of Fmoc-hydrazine in 20 ml of dichloromethane.

2 equivalents of the resulting Fmoc-NHNH—CO-Pnp in dichloromethane and 3 equivalents of DIPEA are added to 1 equivalent of H-Asp(OtBu)-resin and shaken for 1 hour.

After washing with dichloromethane, DMF and again with dichloromethane, Fmoc-NHNH—CO-Asp(OtBu)-resin is obtained.

The Fmoc group is removed using 20% piperidine in DMF.

In the next steps, Fmoc-Arg(Pbf)—OH, Fmoc-Val-OH and Fmoc-D-Phe-OH are coupled on, the Fmoc groups in each case being removed using piperidine before the subsequent coupling.

Fmoc-D-Phe-Val-Arg(Pbf) —NHNH—CO-Asp(OtBu)-resin is obtained.

The peptide is removed from the resin using acetic acid/trifluoroethanol/dichloromethane (1:1:3). Fmoc-D-Phe-Val-Arg(Pbf) —NHNH—CO-Asp(OtBu)—OH is obtained.

A solution of 0.1 mmol of Fmoc-D-Phe-Val-Arg(Pbf)—NHNH—CO-Asp (OtBu)—OH acetate in 50 ml of NMP is slowly added dropwise to a solution of 3 equivalents of TBTU, 3 equivalents of HOBT and 10 equivalents of DIPEA in 50 ml of NMP. After 2 hours, the solvent is removed and the residue is worked up in the customary manner. Cyclo-(Arg-aza-Gly-Asp-D-Phe-Val) is obtained, RT 12.8 min. (20–80, 30 min.); FAB 576.

The compounds
cyclo-(Arg-aza-Gly-Asp-Phe-D-Val), RT 9.5 min. (20–80, 30 min.); FAB 576.
The compounds
cyclo-(Arg-aza-Gly-Asp-D-Phe-NMe-Val), FAB 590;
cyclo-(Arg-aza-Sar-Asp-D-Phe-Val), FAD 590;
cyclo-(Arg-aza-Ala-Asp-D-Phe-Val), FAB 590;
cyclo-(Arg-aza-Gly-Asp-D-Lys-Val);
cyclo-(Arg-aza-Gly-Asp-D-Phe-Lys);
cyclo-(Arg-aza-Gly-Asp-D-Phe-Gly);
cyclo-(Arg-aza-Gly-Asp-D-Phe-Ala);
cyclo-(Arg-aza-Gly-Asp-D-Phe-Phe);
cyclo-(Arg-aza-Gly-Asp-D-Phe-Leu);
cyclo-(Arg-aza-Gly-Asp-D-Phg-Val);
cyclo-(Arg-aza-Gly-Asp-Phe-Gly);
cyclo-(Arg-aza-Gly-Asp-Phe-D-Ala).
are obtained analogously.

The following examples relate to pharmaceutical preparations:

EXAMPLE A: INJECTION VIALS

A solution of 100 g of an active compound of the formula I and 5 g of disodium hydrogenphosphate is adjusted to pH 6.5 using 2 N hydrochloric acid in 3 l of double-distilled water, sterile-filtered, dispensed into injection vials, lyophilized under sterile conditions and aseptically sealed. Each injection vial contains 5 mg of active compound.

EXAMPLE B: SUPPOSITORIES

A mixture of 20 g of an active compound of the formula I is fused with 100 g of soya lecithin and 1400 g of cocoa butter, poured into moulds and allowed to cool. Each suppository contains 20 mg of active compound.

EXAMPLE C: SOLUTION

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water. It is adjusted to pH 6.8, made up to 1 l and sterilized by irradiation. This solution can be used in the form of eye drops.

EXAMPLE D: OINTMENT 500 mg of an active compound of the formula I are mixed with 99.5 g of petroleum jelly under aseptic conditions.

EXAMPLE E: TABLETS

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F: COATED TABLETS

Analogously to Example E, tablets are pressed which are then coated in a customary manner with a coating of sucrose, potato starch, talc, tragacanth and colourant.

EXAMPLE G: CAPSULES 2 kg of active compound of the formula I are dispensed into hard gelatin capsules in a customary manner such that each capsule contains 20 mg of the active compound.

EXAMPLE H: AMPOULES

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

EXAMPLE I: INHALATION SPRAY 14 g of active compound of the formula I are dissolved in 10 l of isotonic NaCl solution and the solution is dispensed into commercially available spray containers having a pump mechanism. The solution can be sprayed into the mouth or nose. One burst of spray (approximately 0.1 ml) corresponds to a dose of approximately 0.14 mg.

What is claimed is:

1. A compound selected from the group consisting of:
   (a) cyclo-(Arg-aza-Gly-Asp-D-Phe-Val) or a physiologically acceptable salt thereof; and
   (b) cyclo-(Arg-aza-Gly-Asp-Phe-D-Val) or a physiologically acceptable salt thereof.

2. A method for preparing a compound according to claim 1, comprising treating a starting material which contains protected amino or hydroxyl groups with a solvolysing or hydrogenolysing agent.

3. A method for preparing a pharmaceutical composition, comprising combining a compound according to claim 1 with at least one additional ingredient, selected from the group consisting of an excipient and an auxiliary.

4. A pharmaceutical composition comprising a compound according to claim 1 and at least one excipient or auxiliary.

5. A method for preparing a physiologically acceptable salt of a basic or acidic compound according to claim 1, comprising treating said basic or acidic compound with an acid or a base, respectively.

6. A method for treating a disease involving an integrin receptor comprising administering to a patient, with said disease, a integrin inhibitory amount of a compound according to claim 1.

7. A method for treating angiogenesis comprising administering to a patient with said angiogenesis a therapeutically effective amount of a compound according to claim 1.

8. A method according to claim 7, wherein said compound is administered in a daily dose of 0.01–2 mg/Kg of body weight.

* * * * *

UNITED STATES PATENT AND TRADEMARK OFFICE
CERTIFICATE OF CORRECTION

PATENT NO. : 6,534,478 B1 Page 1 of 1
DATED : March 18, 2003
INVENTOR(S) : Alfred Jonczyk et al.

It is certified that error appears in the above-identified patent and that said Letters Patent is hereby corrected as shown below:

<u>Title page,</u>
Item [75], Inventors, reads "Darmstadtz" should read -- Darmstadt --
Item [73], Assignee, reads "Mit", should read -- Mit Beschrankter Haftung --

<u>Column 12,</u>
Line 58, reads "a integrin" should read -- an integrin --

Signed and Sealed this

Eighteenth Day of May, 2004

JON W. DUDAS
*Acting Director of the United States Patent and Trademark Office*